US00PP35952P2

(12) United States Plant Patent
Smit

(10) Patent No.: US PP35,952 P2
(45) Date of Patent: Jul. 2, 2024

(54) ***PEPEROMIA* PLANT NAMED 'EC-PEPE-2301'**

(50) Latin Name: *Peperomia caperata*
Varietal Denomination: EC-PEPE-2301

(71) Applicant: Eden Collection, BV, Sappemeer (NL)

(72) Inventor: Obed Smit, Sappemeer (NL)

(73) Assignee: Eden Collection B.V. (NL)

( * ) Notice: Subject to any disclaimer, the term of this patent is extended or adjusted under 35 U.S.C. 154(b) by 0 days.

(21) Appl. No.: 18/373,996

(22) Filed: Sep. 28, 2023

(51) Int. Cl.
*A01H 5/12* (2018.01)
*A01H 5/00* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP32,564 P2 * 12/2020 Smit ..... A01H 6/00
Plt./373

* cited by examiner

*Primary Examiner* — Karen M Redden
(74) *Attorney, Agent, or Firm* — Cassandra Bright

(57) ABSTRACT

A new and distinct cultivar of *Peperomia* plant named 'EC-PEPE-2301' is disclosed, characterized by rosette-shaped compact plant habits. The new variety has heart-shaped leaves with a very dark green leaf upper surface color and red under surface color. The new variety is a *Peperomia*, typically used as an ornamental plant.

2 Drawing Sheets

Figure 1:
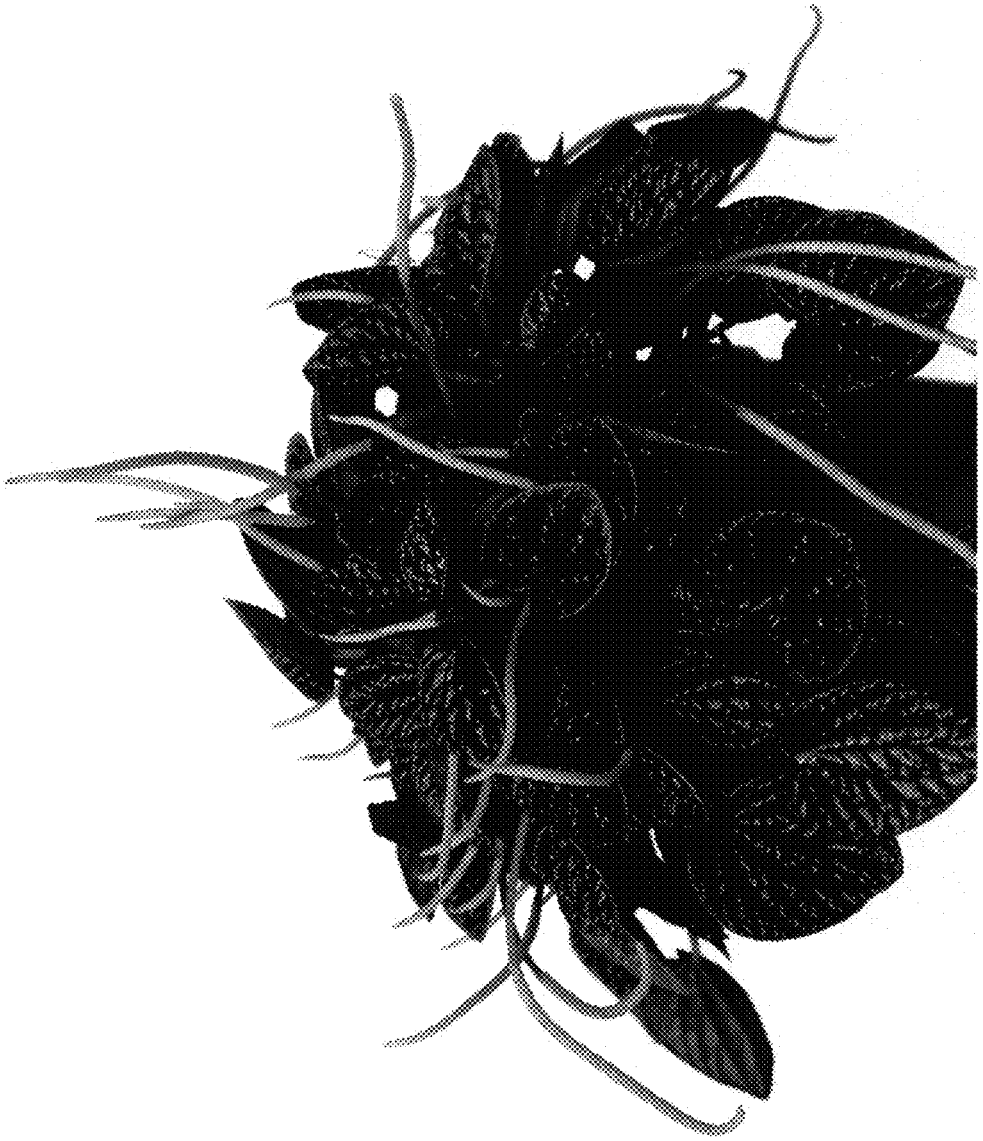

Latin name of the genus and species: *Peperomia caperata.*

Variety denomination: 'EC-PEPE-2301'.

BACKGROUND OF THE INVENTION

The new cultivar is a product of a planned breeding program to produce distinct and better performing *Peperomia* varieties. The new variety was selected as a seedling resulting from the crossing of the seed parent, *Peperomia caperata* '1604', and the pollen parent, *Peperomia caperata* '1612', two unpatented varieties from the inventor's breeding line. The crossing was made by the inventor, Obed J. Smit, a citizen of the Netherlands in 2018. 'EC-PEPE-2301' was selected by the inventor in 2019 at a commercial greenhouse in Sappemeer, the Netherlands.

Asexual reproduction of the new cultivar 'EC-PEPE-2301' was first performed by leaf cuttings in Sappemeer, the Netherlands at a commercial greenhouse in September of 2019, and has shown that the unique features of this cultivar are stable and reproduced true to type through successive generations.

SUMMARY OF THE INVENTION

The cultivar 'EC-PEPE-2301' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2301'. These characteristics in combination distinguish 'EC-PEPE-2301' as a new and distinct *Peperomia* cultivar:

1. Very dark green leaf upper surface color and red under surface color.
2. Heart-shaped leaves.
3. Rosette-shaped compact plant habit.

PARENT COMPARISON

Plants of the new cultivar 'EC-PEPE-2301' are similar to plants of the seed parent, in most horticultural characteristics, however, plants of the new cultivar 'EC-PEPE-2301' differ from in the following characteristics:

1. Foliage color of the upper surface of 'EC-PEPE-2301' is dark green, upper surface color of 8 the seed parent is red.
2. Leaves of the new variety are smaller than leaves of the seed parent variety.
3. Plants of the new variety are small and more compact than plants of the seed parent.

Plants of the new cultivar 'EC-PEPE-2301' are similar to plants of the pollen parent, in most horticultural characteristics, however, plants of the new cultivar 'EC-PEPE-2301' differ in the following characteristics:

1. Foliage color of the upper surface of 'EC-PEPE-2301' is dark green, upper surface color of the pollen parent is a mixture of dark green and light green
2. Leaves of the new variety are heart-shaped. Leaves of the pollen parent are orbicular.
3. Plants of the new variety are smaller with has a more compact habit than plants of the pollen parent.
4. Foliage of the new variety is larger than foliage of the pollen parent.

COMMERCIAL COMPARISON

Plants of the new cultivar 'EC-PEPE-2301' are similar to plants of the commercial variety *Peperomia* 'EC-PEPE- 1904', U.S. Plant Pat. No. 32,564. However, plants of the new cultivar differ in the following characteristics:

1. Leaves of the new variety are smaller than leaves of this comparator.
2. Plants of the new variety are smaller than plants of this comparator.
3. Leaves of the new variety are red on the under surface; leaves of this comparator are light green on the under surface.
4. Leaves of the new variety are very dark green on the upper surface. Leaves of this comparator have two contrasting colors of dark green around main and secondary leaf veins, and silver-grey in between all these veins, as little grey "islands."

Plants of the new cultivar 'EC-PEPE-2301' are similar to plants of *Peperomia* 'Schumi Red', unpatented. However, plants of the new cultivar differ in the following characteristics:

1. Leaves of the new variety are very dark green on the upper surface; leaves of this comparator are red on the upper surface.
2. Plants of the new variety are larger than plants of this comparator.

BRIEF DESCRIPTION OF THE PHOTOGRAPHS

The accompanying photograph in FIG. 1 illustrates in full color a typical plant of 'EC-PEPE-2301' grown in a greenhouse. The plant is approximately 52 weeks of age with inflorescences. Pot size of the photographed plant is 15 cm.

Figure 2:
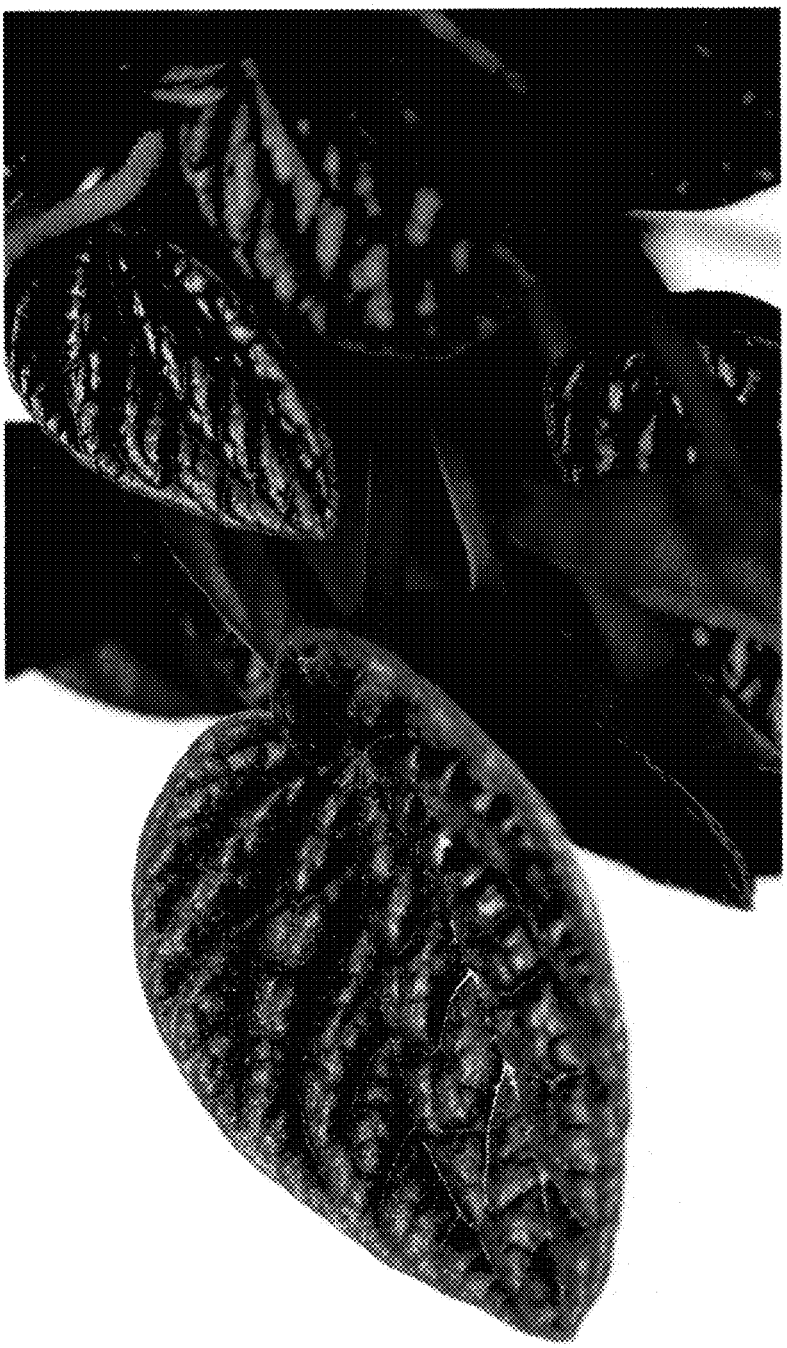

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-2301' plants at 52 weeks of age, grown in a 15 cm pot in a greenhouse in Sappemeer, the Netherlands during December. The growing temperature ranged from 17° C. to 18° C. at night to 19° C. to 21° C. during the day. Measurements and numerical values represent averages of typical flowering types.

Botanical classification: *Peperomia caperata* 'EC-PEPE-2301'.

PROPAGATION

Time to initiate roots: About 21 to 28 days at approximately 21° C.

Time to produce rooted cutting: About 100 to 120 days at 21° C.

Description of roots: Fibrous, fine, moderately dense, freely branching. White in color, not accurately measured with R.H.S. chart.

PLANT

Plant type: Perennial potted plant.

Plant shape: Flattened globular to flattened.

Growth habit: Rosettes of leaves, forming very short, thick stems.

Plant spread: Approximately 39 cm.

Height: 16.2 cm to top of foliar plane. 20.8 cm to top of floral plane.

Growth rate: Moderate.

Plant vigor: Moderate.

Age of plant described: Approximately 52 weeks.

Branching habit: Leaves in rosettes, eventually forming very short, thick stems, branching into lateral rosettes of leaves.

Pinching: Pinching not required.

Number of primary (main) branches per plant: Average 3.

Number of secondary (lateral) branches per plant: Average 3.

Main branches:

*Length*.—Average: 10.1 cm.

*Diameter*.—Average: 0.3 cm.

Internode length: Average: Less than 0.3 cm.

Appearance and shape: Succulent, thick and rounded.

Luster: Matte.

Aspect/angle from vertical: Average angle: 70°.

Strength: Moderately strong.

Color:

*Developing*.—RHS Greyed-Purple N186C blended with Brown 200B.

*Mature*.—RHS Yellow-Green 146A and 146B. Oldest stems 147A.

*At internodes*.—RHS Yellow-Green 146A and 146B.

Pubescence: None.

Plant fragrance: None.

FOLIAGE

Leaf:

*Arrangement*.—Alternate, single.

*Quantity*.—Average 30.

*Average length*.—5.8 cm.

*Average width*.—5.3 cm.

*Shape of blade*.—Cordate.

*Apex*.—Acute.

*Base*.—Cordate.

*Margin*.—Entire. Slightly revolute.

*Texture of top surface*.—Glabrous, smooth, moderately leathery, strongly bullate.

*Texture of bottom surface*.—Glabrous, smooth, moderately leathery.

*Pubescence*.—None.

*Luster, upper side*.—Moderately glossy.

*Luster, under side*.—Slightly glossy, velvety.

*Color*.—Young foliage upper side: RHS Black 203C flushed Yellow-Green 147A. Young foliage under side: RHS Greyed-Purple 183C. Mature foliage upper side: Near RHS Greyed-Green N189A. Adjacent main veins N189A and Black 203A. Mature foliage under side: Greyed-Purple 185A.

*Venation*.—Pattern: Parallel, strongly furrowed. Venation color upper side: Main veins greyed-green to black, a blend of N189A and 203A, lamina reticulately veined N189A to N189B. Venation color under side: RHS Greyed-Purple N186C.

*Petiole*.—Average Length: 8.5 cm. Diameter. 0.35 cm. Texture: Glabrous, smooth. Luster: Both sides slightly glossy. Strength: Low. Color, upper side: RHS Yellow-Green 148C, densely finely-striped Greyed-Purple 183C. Color, under side: RHS Yellow-Green 148C, densely finely-striped Greyed-Purple 183C.

FLOWER

Inflorescence:
*Arrangement*.—Axillary spike.
*Inflorescence type and form*.—Spike.
*Inflorescence height*.—Average: 10.2 cm (excl. peduncle).
*Inflorescence diameter*.—Average: 0.35 cm.
*Quantity of flowers per inflorescence*.—Average approximately 1000 individual flowers per spike.
*Inflorescences per plant*.—Average 30.
Flower bud:
*Flower bud length*.—About 0.2 mm.
*Flower bud diameter*.—About 0.2 mm.
*Flower bud shape*.—Flattened orbicular.
*Flower bud texture*.—Glabrous to slightly velvety.
*Flower bud luster*.—Slightly glossy.
*Flower bud color*.—Near Yellow-Green 145C, slightly tinged Greyed-Purple 185A.
Flower:
*Flower type and form*.—Individual flowers are very small and consist of 1 bract, 2 stamens and a single pistil. No petals or sepals present.
*Fragrance*.—No fragrance.
*Flower height* (*vertical*).—Average: 1.2 mm.
*Flower diameter* (*horizontal*).—Average: 0.7 mm.
*Aspect*.—Outwardly facing.
*Flower longevity on plant*.—Average one month.
*Persistent of self-cleaning*?.—Self-cleaning.
Petals: No petals present.
Calyx: No sepals present; no calyx present.
Peduncles:
*Terminal peduncle length*.—Average: 21.1 cm.
*Terminal peduncle diameter*.—Average: 3.0 mm.
*Peduncle angle to lateral branch axis*.—Average angle: 45°.
*Peduncle strength*.—Moderately weak.
*Peduncle texture*.—Glabrous, smooth.
*Peduncle luster*.—Moderately glossy.
*Peduncle color*.—Yellow-Green 148D, densely finely striped Greyed-Purple 184A.
Pedicels: No pedicels present, individual flowers sessile.
Floral bracts: Below each individual flower a single bract is present, shaped orbicular, average length and width: 0.5 mm, colored near Yellow-Green 147D, slightly tinged Greyed-Purple 185A.

REPRODUCTIVE ORGANS

Androecium:
*Number of stamen per flower*.—Average: 2.
*Filament length*.—Average: 0.3 mm.
*Filament color*.—Near Yellow-Green 145D.
*Anther shape*.—Ovate.
*Anther length*.—Average: 0.3 mm.
*Anther width*.—Average: 0.15 mm.
*Anther color*.—Near Green-White 157A.
*Amount of pollen*.—Low.
*Pollen color*.—White 155A.
Gynoecium:
*Pistil number* (*per flower*).—1.
*Pistil length*.—Average: 0.5 mm.
*Stigma shape*.—Flattened disc.
*Stigma length*.—Average: 0.1 mm.
*Stigma diameter*.—Average: 0.3 mm.
*Stigma color*.—Near RHS Greyed-Green 192D.
*Style length*.—No style visible, stigma sessile.
*Ovary color*.—Near RHS Yellow-Green 144B.

OTHER CHARACTERISTICS

Seeds and fruits: None observed to date.
Disease/pest resistance: No increased nor decreased resistance nor susceptibility to normal diseases and pests of *Peperomia* has been observed.
Temperature tolerance: Tolerates temperatures up to 40° C. Hardy to USDA zones 10 to 12.

What is claimed is:

1. A new and distinct cultivar of *Peperomia* plant named 'EC-PEPE-2301' as herein illustrated and described.

* * * * *